US006973838B2

(12) United States Patent
Denis

(10) Patent No.: US 6,973,838 B2
(45) Date of Patent: Dec. 13, 2005

(54) NON-CONTACTING CRACK SENSOR

(75) Inventor: Kevin L Denis, Elkridge, MD (US)

(73) Assignee: XenotranCorp., Glen Burnie, MD (US)

( * ) Notice: Subject to any disclaimer, the term of this patent is extended or adjusted under 35 U.S.C. 154(b) by 0 days.

(21) Appl. No.: 10/822,075

(22) Filed: Apr. 12, 2004

(65) Prior Publication Data

US 2005/0223812 A1 Oct. 13, 2005

(51) Int. Cl.⁷ .................. G01N 19/08; G01N 29/04
(52) U.S. Cl. .................................... 73/799
(58) Field of Search ............. 73/799, 776, 773; 324/233, 633, 220, 718, 238, 242, 232, 64; 250/227.15

(56) References Cited

U.S. PATENT DOCUMENTS

| 3,497,799 | A | * | 2/1970 | Harmon .................... 324/237 |
| 4,355,281 | A | * | 10/1982 | Toth et al. ................. 324/232 |
| 4,593,245 | A | * | 6/1986 | Viertl et al. ............... 324/238 |
| 5,399,968 | A | * | 3/1995 | Sheppard et al. .......... 324/242 |
| 5,541,510 | A | * | 7/1996 | Danielson ................. 324/233 |
| 5,623,203 | A | * | 4/1997 | Hosohara et al. ......... 324/220 |
| 5,969,260 | A | * | 10/1999 | Belk et al. ................. 73/773 |
| 6,520,024 | B2 | * | 2/2003 | Nihei et al. ................ 73/799 |

* cited by examiner

Primary Examiner—Max Noori
Assistant Examiner—Octavia Davis
(74) Attorney, Agent, or Firm—H. C. Lin Patent Agent

(57) ABSTRACT

A non-contacting sensor based on inductive coupling for detecting failure initiation, and crack propagation in composite materials is disclosed. A very low cost crack sensing transducer or test pattern that can be imbedded into a structural material, interrogated, and powered wirelessly is described. A detection method for interrogating the crack sensor utilizing RF inductive coupling is disclosed. The proposed sensor consists of minimal components resulting in maximum reliability.

6 Claims, 4 Drawing Sheets

NON-CONTACTING CRACK SENSOR

BACKGROUND OF THE INVENTION

1. Field of the Invention

This invention relates to detecting cracks and structural integrity of materials using a remote wireless sensor.

2. Description of the Prior Art

Cracks in structural materials can be detected in many ways. Optical fibers are useful as strain gauges because their long length makes them amendable to detecting strain over wide areas [1]. Disadvantages of using optical fibers are that they are expensive to incorporate into the composite structure, and may additionally degrade material integrity [2]. Frequency response methods can be used to detect a change in stiffness of the structure by measuring a shift in natural frequencies when the structure has been damaged. Ultrasonic and X-Radiography are also used to characterize structural materials, but require access to both the front and back of the structure under test as well as the use of bulky equipment. Composite materials are not isotropic, making correlating results from acoustic detection methods difficult. All of these systems require a means to power the sensor and to physically connect to electrical leads to read out sensory information. In many cases, it is preferred that the sensor be built into the structural material with data read out wirelessly. Additionally, it is also preferred that the sensor can be powered wirelessly, eliminating the need for a power source connection or for an imbedded battery.

Radio-frequency identification RFID type communication systems have recently been integrated with strain gauges [3] to enable wireless transducers. These devices can be fabricated either monolithically with both a Micro-Electro-Mechanical System (MEMS) strain gauge and communications circuitry integrated on the same chip, or a hybrid approach using multiple IC's can be used to integrate the communications circuitry with the transducer. The hybrid approach requires more components and has potentially lower reliability. However, good performance is possible since the sensor and communications circuit fabrication can be done independently. The physical size of the antenna requires that it be implemented in a hybrid approach. In either implementation, these systems have a number of deficiencies, including large size, reduced reliability, and high cost.

In general, any system that must communicate through RF wireless communications requires the use of an antenna. In this invention, a device which serves the dual purpose of antenna and crack sensing gauge is described. The goal is to provide a very low cost sensing device that provides reliable material integrity information.

SUMMARY OF THE INVENTION

The object of this invention is to remotely detect cracks in materials. Another object of this invention is to provide a sensor which serves the dual purpose of antenna and crack sensing gauge. Still another object of the present invention is to provide a very low cost sensing device that provides reliable material integrity information.

The crack sensing system consists of three components, a crack sensor, a wireless reader, and a computer for tracking and recording data.

The crack sensor is affixed on or within the structural material and is powered wirelessly from a remote reader. In one embodiment, the crack sensor consists of a number of concentric metal rings patterned on an insulating substrate such as Mylar or polyimide. The rings are designed to break when a crack within the structural material propagates below or above them.

The remote reader consists of an antenna and a measurement circuit. The antenna inductively couples with the sensor when the sensor enters within range of the reader's antenna. The measurement circuit then determines the structural integrity of the material by determining if any of the rings of the sensor have broken. The reader can then be interfaced with a computer to track integrity of the materials.

In another embodiment the crack sensor consists of an array of breakable conductors connected to an adjacent embedded antenna. The integrity of the array can be determined by remotely measuring the impedance of the embedded circuit.

DETAILED DESCRIPTION OF THE PREFERRED EMBODIMENT

Figure 1:
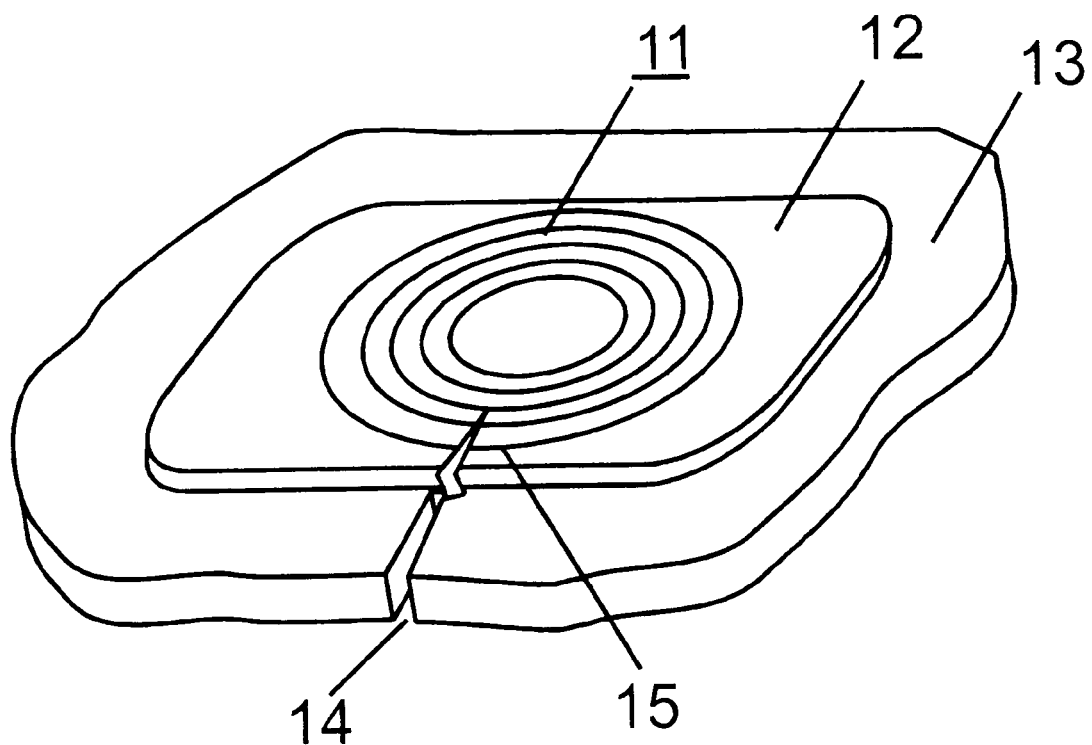
FIG. 1 shows a drawing of the crack sensor.

FIG. 1 shows the preferred embodiment of the crack sensor. The sensor consists of a number of concentric metal rings 11 that are built upon an insulating substrate 12. The rings and substrate are bonded to the structural material 13[,] under test. The rings are designed to break when a crack in the structural material propagates below them. This is accomplished by ensuring that for a critical crack size the stress within the structural material exceeds the critical strain energy release rate of the adhesive/crack sensor system. The strain energy release rate of the sensor system therefore must be lower than that of the structural material. First, to ensure that cracks couple with the sensor, allowing detection, and second, to reduce the probability of a crack nucleation site arising in the sensor from propagating to the composite matrix. If a crack 14 is produced in the structural material, one or more of the metal rings such as 15 will break causing an open circuit in that ring.

Figure 2:
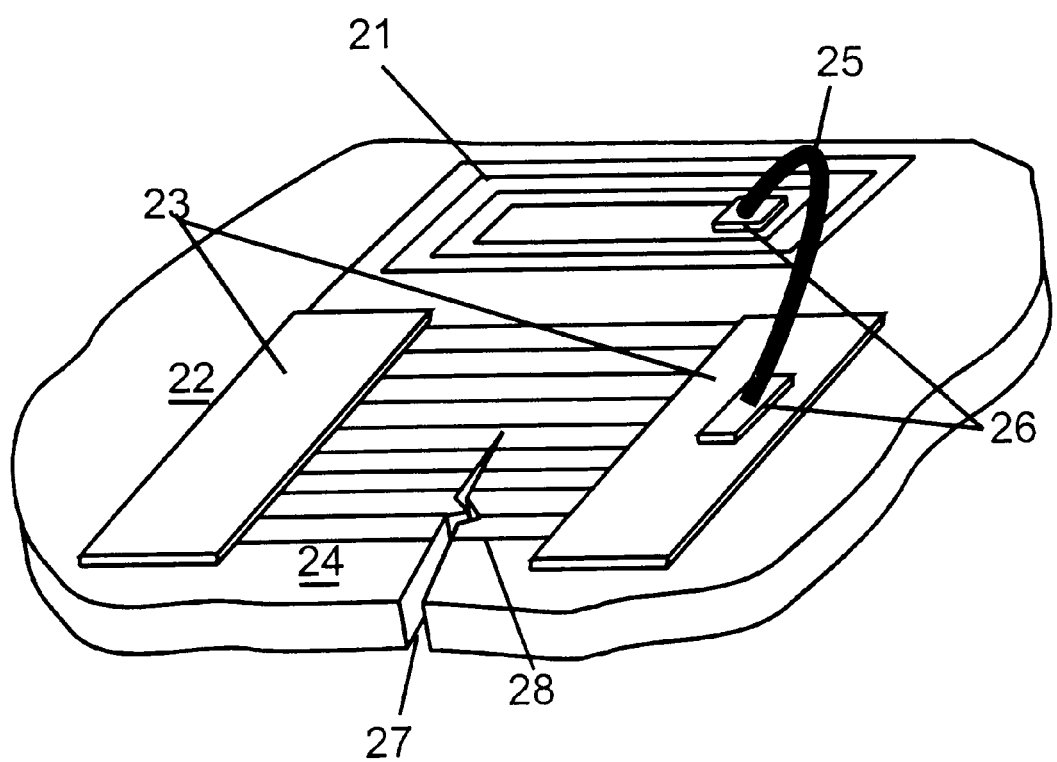
FIG. 2 shows a drawing of an alternative configuration of the crack sensor.

In an alternative embodiment of the invention, shown in FIG. 2, the sensor consists of a multi-turn coil 21 serving as antenna. Here the antenna is designed not to break in the presence of cracks in the structural material. The antenna coil is connected in series with a crack sensor 22, consisting of contacts 23 and resistive elements 24. Connecting bridge 25 is attached to metal contacts 26. In order to insulate the bridge from the coil, the bridge of metal may be placed on the backside of the substrate and connected via throughholes to the circuit, or alternatively, a dielectric layer may be placed under the metal bridge. The resistance of the crack sensor will change when a crack 27 propagates through the material under the sensor. This causes one or more wires such as 28 to break, producing an increase in impedance between metal contacts 23. In this embodiment, the reader detects the presence of a crack by measuring the Q or quality factor of the circuit. The quality factor is a measure of the sharpness of the curve that results when the voltage or current amplitude is measured as a function of frequency and the system goes through a resonant frequency. The quality factor does not depend on the mutual inductance of the reader and sensor antennas and therefore is independent of the distance and angle between the two devices. This fact reduces ambiguities in the measurement.

Figure 3:
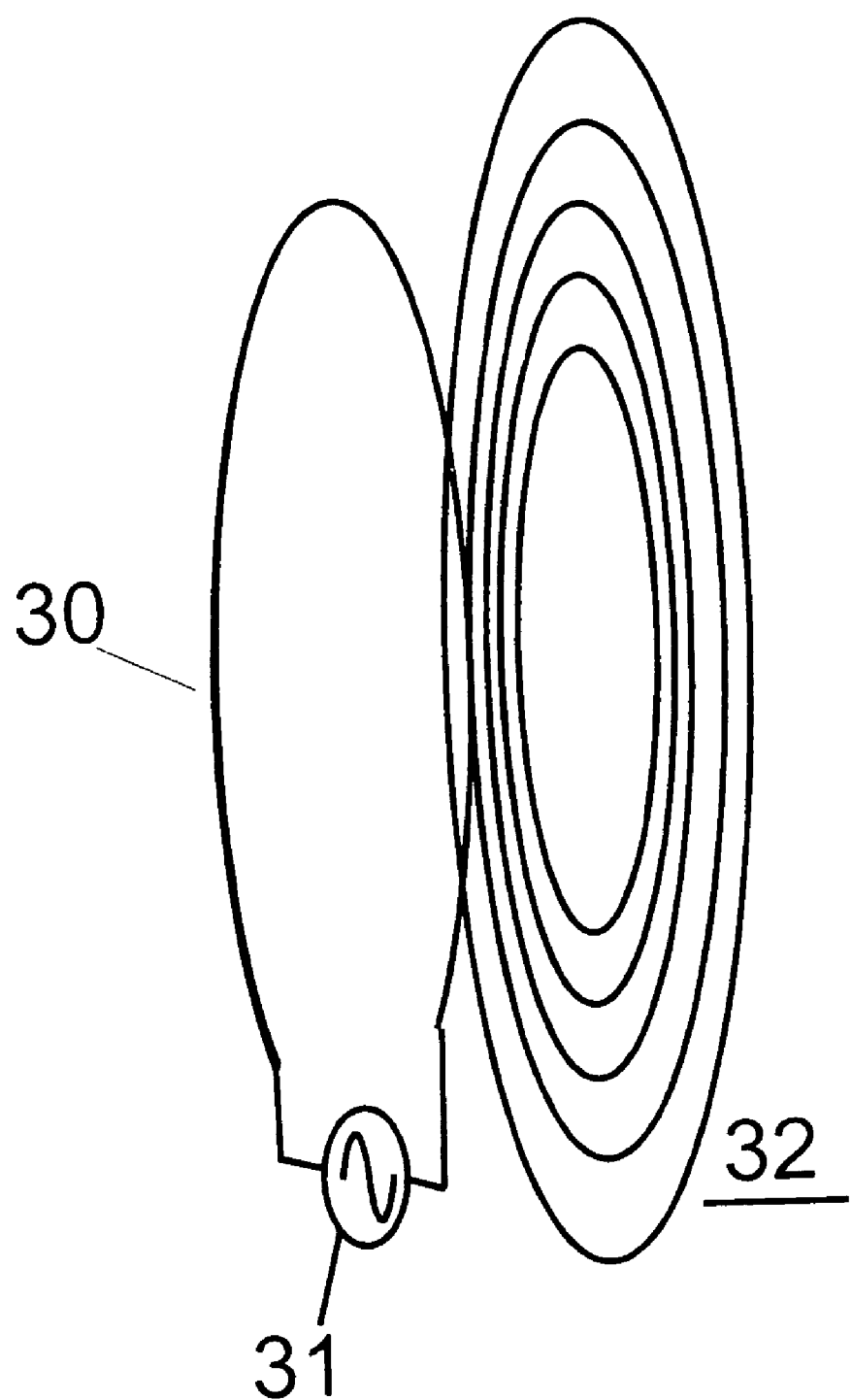
FIG. 3 depicts the sensor and reader antenna.

The crack sensor and reader system is designed to operate in the near field region where the distance between them is much smaller than the wavelength of the transmitter. FIG. 3 shows the reader coil 30 and the sensor coil 32, excited by power source 31. The reader antenna and the sensor coil can be modeled as an inductive transfer system. The sensor and reader system is similar to a transformer, where the voltage in the primary is transferred to a voltage in the secondary through inductive coupling. Each of the loops in the crack sensor will have a mutual inductance with every other loop of the crack sensor as well as with the primary antenna. Additionally, each of the loops in the crack sensor will have its own distinct self-inductance. The equivalent inductance of the sensor system will be a function of these self and mutual inductances. When a crack in the material under test causes one of the loops to break, the equivalent inductance of the system will be modified. By measuring the effective inductance of the crack sensor one can quickly determine the integrity of the structural material.

Figure 4:
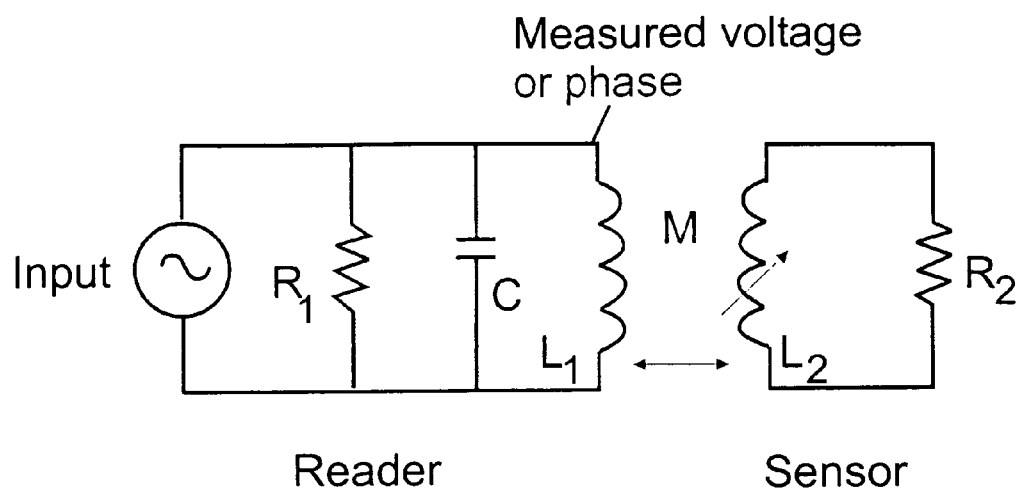
FIG. 4 shows a circuit diagram of the sensor and reader electronics.

FIG. 4 shows a circuit diagram depicting the system. In this figure, the reader antenna is depicted as an LCR tank circuit that is coupled to a series LR circuit secondary. The AC input voltage is used to excite the circuit, which forms a resonant system. At low frequencies, the impedance of the capacitor dominates the impedance of the circuit. At very high frequencies, the impedance of the equivalent inductance dominates the circuit. At the resonant frequency of the system the impedance of the inductor and the capacitor are equal and the resonant frequency is given by $f_{res}=1/\sqrt{LC}$, where L is the effective inductance of the primary and the secondary which is a function of the number of rings in sensor that are intact. Measurement of the resonant frequency of the system thus gives a measure of the existence and extent of a crack in the material.

The effective inductance will also depend on a variety of other factors including the distance between the reader antenna and the sensor as well as the angle between the plane of the sensor and that of the reader. In order for the reader to determine whether the sensor has detected a crack, it must be designed to take into consideration these effects. The distance between sensor and antenna are determined independently by including a proximity transducer in the reader electronics, while the angle is determined by using two antennas at an angle to each other in the reader. In this measurement, the inductive coupling is measured using the first antenna, then that antenna is open-circuited and the measurement is repeated for the second antenna. If the distance between the antenna and the sensing element is known along with the angle between the two reader antennas, one can cancel the dependence of angle between the reader antenna and the sensor on the measurement.

Figure 5:
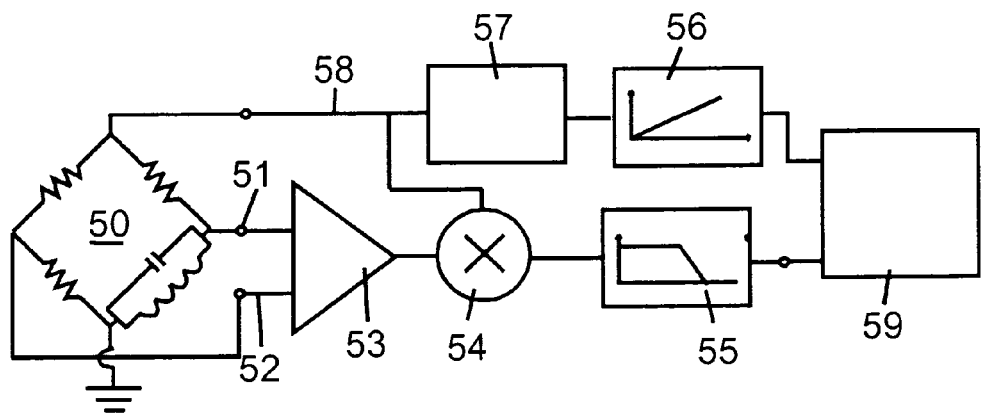
FIG. 5 shows a block diagram of the electronics system for the reader electronics.

Detection of a resonant frequency shift can be done by using the circuit depicted schematically in FIG. 5. Here it is assumed that the primary tank is connected in a bridge circuit 50. When the voltage ramp circuit 56 is triggered, it causes the voltage-controlled oscillator 57, which serves as the excitation to the bridge circuit 50, to scan the frequency of its output signal 58. The differential output signal 51, 52 from the bridge is amplified by amplifier 53 and fed to multiplier 54. The multiplier multiplies the amplified output signal from the bridge by the signal from the voltage-controlled oscillator. Since the two signals are at the same frequency with only a difference in phase, the output from the multiplication operation will consist of a DC component plus a component at twice the excitation frequency. The doubled frequency is removed by the low pass filter 55. The final DC signal and the voltage ramp are digitized and processed for display in a digital processor 59. The digital processor 59 consists of two analog-to-digital converters for converting both the DC voltage and the ramp signal to digital values. The digital processor 59 also includes a proximity sensor that measures the distance between the sensor and the antenna, and provides a digital signal proportional to the distance. The DC signal from the low pass filter 55 is proportional to the magnitude of the differential output signal 51, 52 from the bridge circuit 50. The digitized ramp signal corresponds to the frequency applied to the bridge when the sense amplitude is measured. The differential signal maximum corresponds to the resonant frequency. The mutual coupling between the crack sensor and the antenna depends on the distance between the sensor and the antenna. The digital processor uses this distance information along with the differential signal maximum and the frequency, at which the maximum is measured, to calculate the inductance of the crack sensor and thus to determine the integrity of material. Alternatively, I the low pass filter 55 is removed, the digital processor 59 can be made to count the doubled frequency while measuring the magnitude of the signal at that frequency. The frequency at which the maximum is determined corresponds to twice the resonant frequency of the system and corresponding distance information can be used to determine the integrity of the material The system in FIG. 5 can also be applied to measure the Q in the second embodiment of the invention. Here the width (in frequency) of the oscillation peak is measured and is related back to the amount of resistance in the circuit.

This invention can be used in a variety of applications where structural integrity of materials is required. Aircraft components made from composite materials are routinely examined for defects. This invention can be used to give a quick objective assessment of material integrity. Manufacturers of composite materials could embed sensors within the material to qualify manufacturing processes. Additionally, the sensors could be imbedded at critical areas in structures such as bridges and buildings allowing them to be routinely monitored.

While the preferred embodiments of the invention have been described, it will be apparent to those skilled in the art that various modifications may be made to the embodiments without departing the spirit of the invention. Such modifications are all within the scope of the present invention.

What is claimed is:

1. A sensing system for detecting cracks and structural integrity of material, comprising:
    a material under test;
    an insulating substrate mounted on said material;
    a test pattern deposited on said insulating substrate, forming an element of an oscillator for transmitter to radiate a radio frequency RF signal, and
    a remote sensing circuit to detect any deviation of the received signal from said transmitter as a measure of the presence of any crack in the material under test,
    wherein said pattern is a bank of resistors and any breakage of said resistors due to propagation of a crack in the underlying material under test amplitudes-modulates the oscillator.

2. The sensing system as described in claim 1, wherein the resistors are used to determine the quality factor of a LC tank circuit.

3. The sensing system as described in claim 2, wherein the signal strength of the transmitter depends on the integrity of the resistors.

4. The sensing system as described in claim 3, wherein said remote sensing circuit is a detector, which can demodulate both FM signal and AM signal.

5. A sensing system for detecting cracks and structural integrity of material, comprising:
   a material under test;
   an insulating substrate mounted on said material;
   a test pattern deposited on said insulating substrate, forming an element of an oscillator for a transmitter to radiate a radio frequency RF signal; and
   a remote sensing circuit to detect any deviation of the received signal from said transmitter as a measure of the presence of any crack in the material under test,
   wherein the test pattern is an inductor and any breakage of the inductor due to propagation of a crack in the underlying material under test frequency-modulates the oscillator,
   wherein said inductor forms a LC tank circuit in the transmitter and any breakage of the inductor causes the resonant frequency of the oscillator to shift,
   wherein said remote sensing circuit is a phase/frequency detector to detect the phase/frequency deviation of the received signal,
   wherein the said radiated signal from said transmitter is picked up a parallel LC tank circuit to develop an RF voltage, and
   wherein said RF voltage is detected by a detector comprising:
      a bridge circuit to output said RF voltage,
      an amplifier to amplify said RF voltage,
      a voltage controlled oscillator (VCO) which is controlled a voltage ramp to generate a sweep frequency,
      a multiplier to multiply the said RF voltage with the sweep frequency signal from said VCO and to yield a DC and double frequency output when the sweep frequency coincides with said RF signal
      a DC voltage to measure the AM signal from said transmitter to indicate any amplitude deviation, hence the presence of the crack, when the resistance bank is used as a the test pattern, and
      a frequency counter to count the double frequency of an FM signal to measure the frequency deviation and hence the presence of the crack when an inductor is used as the test pattern.

6. A method of sending a a crack of material, comprising the steps of:
   depositing an insulating layer on a material to be tested;
   depositing a test pattern of an electronic element on said insulating layer as a component of an oscillator;
   modulating the oscillator with deviations of said electronic element value due to crack in said material propagating to said test pattern;
   remote sensing an RF signal to measure the presence of any said crack,
      wherein said test pattern is a resistance bank, which controls the quality factor of LC tank circuit of said oscillator, and oscillator is amplitude modulated by said crack.

* * * * *